US008802019B2

(12) United States Patent
Olbert et al.

(10) Patent No.: US 8,802,019 B2
(45) Date of Patent: *Aug. 12, 2014

(54) REACTOR FOR CARRYING OUT AN AUTOTHERMAL GAS-PHASE DEHYDROGENATION

(75) Inventors: Gerhard Olbert, Dossenheim (DE); Ulrike Wegerle, Worms (DE); Grigorios Kolios, Neustadt (DE); Albena Kostova, Mannheim (DE); Jasmina Kessel, Mannheim (DE); Alexander Weck, Freinsheim (DE); Alireza Rezai, Mannheim (DE)

(73) Assignee: BASF SE, Ludwigshafen (DE)

( * ) Notice: Subject to any disclaimer, the term of this patent is extended or adjusted under 35 U.S.C. 154(b) by 203 days.

This patent is subject to a terminal disclaimer.

(21) Appl. No.: 13/331,362

(22) Filed: Dec. 20, 2011

(65) Prior Publication Data

US 2012/0157737 A1    Jun. 21, 2012

Related U.S. Application Data

(60) Provisional application No. 61/425,280, filed on Dec. 21, 2010, provisional application No. 61/491,911, filed on Jun. 1, 2011, provisional application No. 61/562,454, filed on Nov. 22, 2011.

(51) Int. Cl.
*B01J 19/00* (2006.01)
*B01J 8/00* (2006.01)
*B01J 8/02* (2006.01)
*B01J 8/04* (2006.01)
*B01J 35/02* (2006.01)
*C07C 13/00* (2006.01)
*C07C 5/32* (2006.01)
*C07C 5/42* (2006.01)

(52) U.S. Cl.
USPC ........... 422/198; 422/129; 422/211; 422/240; 422/600; 422/630; 422/649; 585/350; 585/379; 585/380

(58) Field of Classification Search
USPC ......... 422/129, 198, 211, 240, 600, 620, 621, 422/625, 628, 630, 631, 633, 644, 649; 585/350, 379, 380, 500, 601, 616, 654
See application file for complete search history.

(56) References Cited

U.S. PATENT DOCUMENTS 7,034,195 B2    4/2006  Schindler et al.
7,388,106 B2 *  6/2008  Klanner et al. ............ 562/512.2

(Continued)

FOREIGN PATENT DOCUMENTS

DE        4026566 A1       2/1992
EP        0081021 A1       6/1983
WO    WO-2011/067235      6/2011

OTHER PUBLICATIONS

International Search Report for PCT/EP2011/072636, mailed Feb. 17, 2012.

*Primary Examiner* — Natasha Young
(74) *Attorney, Agent, or Firm* — Drinker Biddle & Reath LLP

(57) ABSTRACT

A reactor includes an essentially horizontal cylinder for carrying out an autothermal gas-phase dehydrogenation of a hydrocarbon-comprising gas stream using an oxygen-comprising gas stream to give a reaction gas mixture over a heterogeneous catalyst configured as monolith. The interior of the reactor is divided by a detachable, cylindrical or prismatic housing, which is arranged in the longitudinal direction of the reactor and is gastight in the circumferential direction, into an inner region having one or more catalytically active zones, each having a packing composed of monoliths stacked on top of one another, next to one another and behind one another and before each catalytically active zone in each case a mixing zone having solid internals are provided and into an outer region, which is supplied with an inert gas, arranged coaxially to the inner region. A heat exchanger is connected to the housing at one end of the reactor.

24 Claims, 3 Drawing Sheets

(56) References Cited

U.S. PATENT DOCUMENTS

Figure 3:
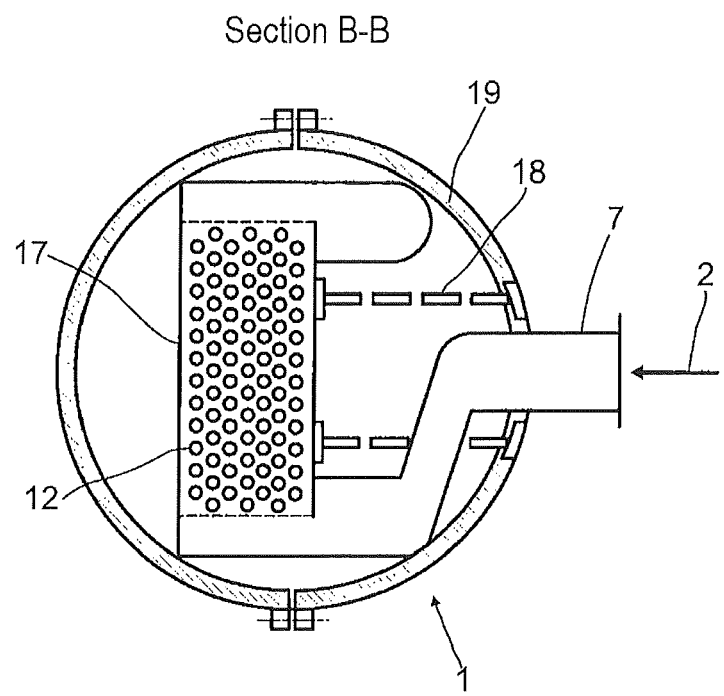

| | | | |
|---|---|---|---|
| 7,497,881 B2 * | 3/2009 | Burch et al. | 48/127.9 |
| 2008/0119673 A1 | 5/2008 | Hechler et al. | |
| 2009/0292030 A1 | 11/2009 | Casey et al. | |
| 2011/0130607 A1 | 6/2011 | Kolios et al. | |
| 2013/0035529 A1 * | 2/2013 | Olbert et al. | 585/380 |
| 2013/0035531 A1 * | 2/2013 | Olbert et al. | 585/443 |

* cited by examiner

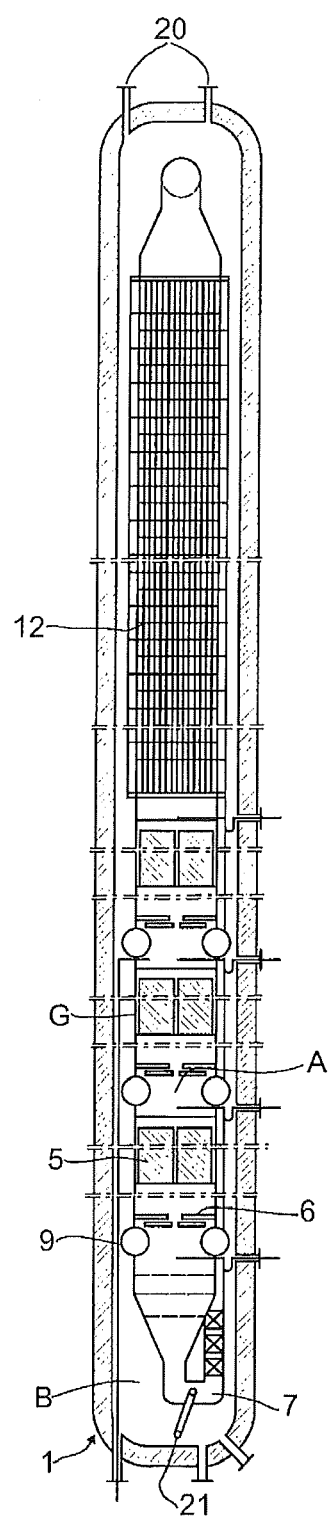
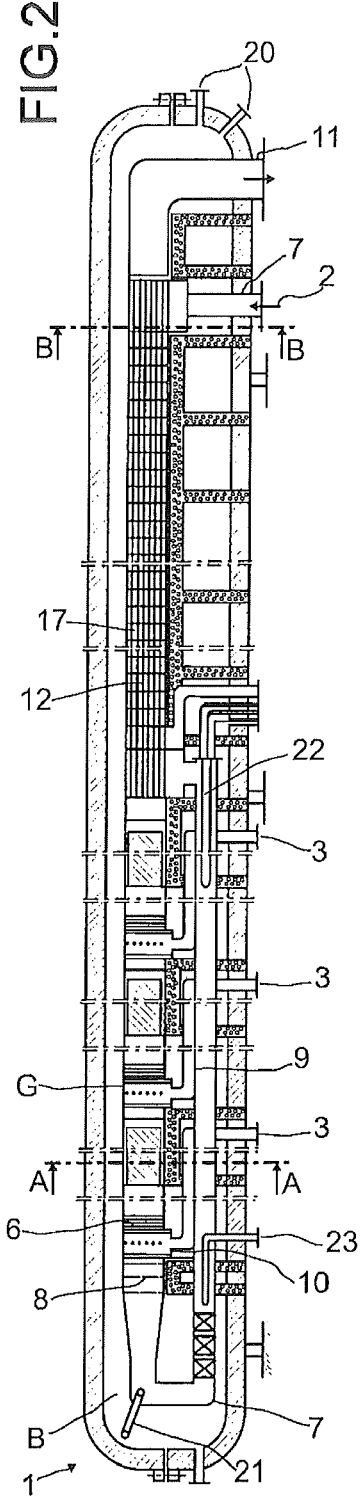

Section B-B

Section A-A

REACTOR FOR CARRYING OUT AN AUTOTHERMAL GAS-PHASE DEHYDROGENATION

This patent application claims the benefit of pending US provisional patent application Ser. No. 61/425,280 filed Dec. 21, 2010, Ser. No. 61/491,911 filed Jun. 1, 2011 and Ser. No. 61/562,454 filed Nov. 22, 2011 incorporated in its entirety herein by reference.

The invention relates to a reactor for carrying out autothermal gas-phase dehydrogenations using a heterogeneous catalyst configured as a monolith and also a process using the reactor.

Ceramic or metallic monoliths have become established as catalyst supports for noble metal catalysts in mobile and stationary offgas purification. The channels offer a low resistance to flow and at the same time uniform accessibility to the outer catalyst surface for gaseous reaction media. This is advantageous compared to disordered beds in which a large pressure drop results from numerous deflections in the flow around the particles and the catalyst surface may not be uniformly utilized. The use of monoliths is generally of interest for catalytic processes having high volume flows under adiabatic reaction conditions at high temperatures. In chemical process technology, these features apply particularly to dehydrogenation reactions which occur in the temperature range from 400° C. to 700° C.

Progress in catalyst technology has made selective combustion of the dehydrogenation hydrogen in the presence of hydrocarbons possible, as described, for example, in U.S. Pat. No. 7,034,195. Such a mode of operation is referred to as autothermal dehydrogenation and allows dehydrogenation reactors to be heated directly, so that complicated apparatuses for indirect preheating and intermediate heating of the reaction mixture become unnecessary. One such process is described, for example, in US 2008/0119673. However, this process has the serious disadvantage that the dehydrogenation is carried out over a heterogeneous catalyst in pellet form: the high flow resistance of beds of pellets requires a large reactor cross section and a correspondingly low flow velocity in order to limit the pressure drop in the catalytically active layer. This disadvantage is compensated by a very complicated apparatus for introducing and distributing the oxygen, which impairs the advantage of autothermal dehydrogenation.

The European patent application (corresponding to 08/1021EP), which is not a prior publication, discloses a reactor and also a process for the autothermal gas-phase dehydrogenation of hydrocarbons using heterogeneous catalysts configured as monoliths, which ensure safe control of the combustible reaction media at high reaction temperatures, frequently in the range from about 400 to 700° C., and also easy accessibility and handling of the monoliths, in particular on equipping the reactor and also on changing the catalyst.

The European patent (corresponding to 08/1021EP) provides a reactor in the form of an essentially horizontal cylinder for carrying out an autothermal gas-phase dehydrogenation of a hydrocarbon-comprising gas stream by means of an oxygen-comprising gas stream to give a reaction gas mixture over a heterogeneous catalyst configured as monolith, wherein the interior of the reactor is divided by a detachable, cylindrical or prismatic housing G which is arranged in the longitudinal direction of the reactor and is gastight in the circumferential direction and open at two end faces of the housing into an inner region A having one or more catalytically active zones, in which a packing composed of monoliths stacked on top of one another, next to one another and behind one another and before each catalytically active zone in each case a mixing zone having solid internals are provided, and an outer region B arranged coaxially to the inner region A, with one or more feed lines for the hydrocarbon-comprising gas stream to be dehydrogenated into the outer region B, deflection of the hydrocarbon gas stream to be dehydrogenated at one end of the reactor and introduction via a flow equalizer into the inner region A, with one or more feed lines which can be regulated independently of one another, where each feed line supplies one or more distribution chambers for the oxygen-comprising gas stream into each of the mixing zones and with a discharge line for the reaction mixture of the autothermal gas-phase dehydrogenation at the same end of the reactor as the feed line for the hydrocarbon gas stream to be dehydrogenated.

At the end of the reactor at which the discharge line for the reaction gas mixture from the autothermal gas-phase dehydrogenation is arranged, it is advantageous to provide a shell-and-tube heat exchanger having a bundle of tubes through which the reaction gas mixture from the autothermal gas-phase dehydrogenation is passed and also intermediate spaces between the tubes through which the hydrocarbon-comprising gas stream to be dehydrogenated is passed in countercurrent to the reaction mixture from the autothermal gas-phase dehydrogenation.

However, the above reactor has disadvantages from a safety point of view because the lines carrying oxygen lead through the space in which the hydrocarbon-comprising stream circulates. In the case of a leakage through a crack in the pipe, ignition/explosion can therefore occur. In addition, in the embodiment having a shell-and-tube heat exchanger which projects out from the outer wall of the reactor, sealing at this point is only unsatisfactorily solved.

It was therefore an object of the invention to provide an improved reactor which overcomes the above disadvantages.

The object is achieved by a reactor in the form of a horizontal cylinder or prism for carrying out an autothermal gas-phase dehydrogenation of a hydrocarbon-comprising gas stream by means of an oxygen-comprising gas stream to give a reaction gas mixture over a heterogeneous catalyst configured as monolith, where the interior of the reactor is divided by a detachable, cylindrical or prismatic, gastight housing G which is arranged in the longitudinal direction of the reactor into an inner region A having one or more catalytically active zones, in each of which a packing composed of monoliths stacked on top of one another, next to one another and behind one another and before each catalytically active zone in each case a mixing zone having solid internals are provided, and an outer region B arranged coaxially to the inner region A, and a heat exchanger is provided at one end of the reactor connected to the housing G, with one or more feed lines for the hydrocarbon-comprising gas stream to be dehydrogenated, with one or more feed lines which can be regulated independently of one another, where each feed line supplies one or more distribution chambers, for the oxygen-comprising gas stream into each of the mixing zones and with a discharge line for the reaction gas mixture of the autothermal gas phase dehydrogenation, wherein the outer region B is supplied with a gas which is inert under the reaction conditions of the autothermal gas-phase dehydrogenation and the hydrocarbon-comprising gas stream to be dehydrogenated is introduced via a feed line into the heat exchanger, is heated by means of the reaction gas mixture in countercurrent by indirect heat exchange and conveyed further to the end of the reactor opposite the heat exchanger, redirected there, introduced via a flow equalizer into the inner region A and mixed with the oxygen-comprising gas stream in the mixing zones, whereupon the autothermal gas-phase dehydrogenation takes place in the inner region A of the reactor.

Thus, a reactor having an outer reactor wall, i.e. a pressure-bearing shell which is not contacted by a medium, neither by the hydrocarbon-comprising stream nor by the oxygen-comprising stream, is provided according to the invention.

A cylindrical or prismatic housing G is provided in the longitudinal direction of the reactor and divides the interior of the reactor into an inner region A and an outer region B arranged concentrically around the inner region A.

The outer region B is supplied with a gas which is inert under the reaction conditions of the autothermal gas-phase dehydrogenation, i.e. a gas or gas mixture which does not participate directly in the reaction of the autothermal gas-phase dehydrogenation, in particular selected from among water, carbon dioxide, nitrogen and noble gases or mixtures thereof. Steam is preferably used as gas which is inert under the reaction conditions of the autothermal gas-phase dehydrogenation since it can be separated off from the reaction gas mixture again in a simple way, by condensation.

The gas which is inert under the reaction conditions of the autothermal gas-phase dehydrogenation is preferably passed as purge gas stream through the inner region A at a low mass flow compared to the mass flow of the hydrocarbon-comprising gas stream, i.e. a mass flow of from $1/5$ to $1/100$, preferably a mass flow of from $1/10$ to $1/50$, based on the mass flow of the hydrocarbon-comprising gas stream, under a low gauge pressure of from 2 to 50 mbar, preferably from 25 to 30 mbar, based on the pressure in the inner region A.

The purge gas stream can advantageously be conveyed through the outer region B by being introduced into the outer region B of the reactor via one or more feed lines at one end of the reactor and being conveyed further into the inner region A of the reactor at the opposite end of the reactor, preferably via one or more connecting line(s) which are advantageously arranged at an angle other than 90° to the feed line for the hydrocarbon-comprising gas stream to be dehydrogenated.

The one or more connecting line(s) which conduct the purge gas stream from the outer region B into the inner region A are preferably configured so that they are backflow-free, for example by means of a helical shape. The inlet from the outer region B into the connecting line for the purge gas stream should preferably be arranged as high as possible in the outer region B of the reactor.

The purge gas stream continually flushes the outer region B of the reactor and keeps it free of components of the reaction gas mixture.

A heat exchanger, which can, in particular, be a shell-and-tube heat exchanger or a plate heat exchanger, is connected at one end of the housing G, in the case of a shell-and-tube heat exchanger, the connection between this and the housing G is configured so that the inner region A communicates with the interior of the tubes of the shell-and-tube heat exchanger. In the case of a plate heat exchanger, the inner region A of the reactor communicates with the gaps between the plates of the plate heat exchanger.

The intermediate space between the tubes of the shell-and-tube heat exchanger or between in each case two metal sheets welded together to form a heat exchange plate of the plate heat exchanger is connected, via a line which leads to the end of the reactor opposite the heat exchanger and is redirected there, to the end of the housing G opposite the heat exchanger and thus to the inner region of the reactor so as to form a gastight seal from the outer region B.

The hydrocarbon-containing stream is conveyed through the intermediate space between the tubes of the shell-and-tube heat exchanger or, in the case of a plate heat exchanger, through the intermediate spaces between the metal sheets which in each case form a heat exchanger plate, heated by the product gas stream circulating in countercurrent through the tubes or through the gaps between the plates of the plate heat exchanger, conveyed to the opposite end of the reactor, redirected there and introduced into the inner region A of the housing.

The autothermal gas-phase dehydrogenation takes place over a heterogeneous catalyst which is present in the form of monoliths.

For the present purposes, a monolith is a one-piece, parallelepipedal block having a plurality of continuous channels which are arranged parallel to one another and have a narrow cross section in the range from about 0.5 to 4 mm.

The monoliths are preferably formed by a ceramic material as support material onto which a catalytically active layer has been applied, preferably by the washcoating process.

The most usual material for monolithic structures is cordierite (a ceramic material comprising magnesium oxide, silicon oxide and aluminum oxide in a ratio of 2:5:2). Other materials of which commercially available monolithic structures are made are metals, mullite (mixed oxide of silicon oxide and aluminum oxide, ratio=2:3) and silicon carbide. These materials have, like cordierite, a low specific BET surface area (BET=Brunauer, Emmet and Teller) (e.g. typically 0.7 $m^2/g$ for cordierite).

Monolithic ceramic elements having cell counts of 25-1600 cpsi (cells per square inch, corresponds to a cell size of 5-0.6 mm) can be obtained. Use of a higher cell count increases the geometric surface area, so that the catalyst can be used more efficiently. Disadvantages of higher cell counts are a somewhat more difficult production process, difficult washcoat coating and a higher pressure drop over the reactor. However, the pressure drop remains very low for monoliths having a high cell count compared to a reactor packed with random packing elements (generally a factor of 10 lower), which can be attributed to the straight channels in the monolith.

To produce monolithic ceramic elements, it is possible to produce a mixture of talc, clay and an aluminum oxide-supplying component and silicon oxide, mix the mixture to form a molding composition, shape the mixture, dry the raw product and heat it at a temperature of from 1200 to 1500° C. to give a ceramic which comprises mainly cordierite and has a low coefficient of thermal expansion. Generally speaking, a paste having appropriate rheological properties and an appropriate rheological composition can be extruded to form a monolithic support. The paste generally comprises a mixture of ceramic powders of suitable size, inorganic and/or organic additives, solvent (water), peptizing agent (acid) to set the pH and a permanent binder (colloidal solution or sol). The additives can comprise a plasticizer or a surfactant for adjusting the viscosity of the paste or a temporary binder which can later be burned out. Glass or carbon fibers are sometimes added to increase the mechanical strength of the monolith. The permanent binder should improve the internal strength of the monolith.

Cordierite monoliths can be produced from a batch comprising talc, kaolin, calcined kaolin and aluminum oxide and together give a chemical compound composed of from 45 to 55% by weight of $SiO_2$, from 32 to 40% by weight of $Al_2O_3$ and from 12 to 15% by weight of MgO. Talc is a material which consists mainly of magnesium silicate hydrate, $Mg_3Si_4O_{10}(OH)_2$. The talc can, depending on the source and purity, also be associated with other minerals such as tremolite $(CaMg_3(SiO_3)_4)$, serpentine $(3MgO.2SiO_2.2H_2O)$, anthophyllite $(Mg_7(OH)_2(Si_4O_{11})_2)$, magnesite $(MgCO_3)$, mica and chlorite.

Monoliths composed of other materials such as SiC, $B_4C$, $Si_3N_4$, BN, AlN, $Al_2O_3$, $ZrO_2$, mullite, Al titanite, $ZrB_2$, sialon, perovskite, carbon and $TiO_2$ can also be produced by extrusion.

Parameters in the extrusion which are important in respect of the properties of the monolith products are not only the quality of the nozzle and the type and properties of the materials used for producing the formable mixture but also the additives added, the pH, the water content and the force used in extrusion. The additives employed in extrusion are, for example, celluloses, $CaCl_2$, ethylene glycols, diethylene glycols, alcohols, wax, paraffin, acids and heat-resistant inorganic fibers. Apart from water, it is also possible to use other solvents such as ketones, alcohols and ethers. The addition of additives can lead to improved properties of the monoliths, for example formation of microcracks, which improves the thermal shock resistance, improved porosity and better absorption capacity and increased mechanical strength or low thermal expansion.

The bare monolithic structure is coated with a catalyst support layer comprising one or more ceramic oxides or a catalyst layer comprising the catalytically active metals and the optional further (promoter) elements already supported on the ceramic oxide support material, with the coating being produced by a washcoat coating method.

The macroporous structure of ceramic monoliths aids the anchoring of the washcoat layer. The way of coating with the washcoat can be carried out by two methods: the macroporous support can be (partly) filled with the washcoat material having a large surface area or a washcoat can be deposited as a layer in the pores of the ceramic support. The filling of the pores leads to a very strong interaction between monolith and washcoat since the major part of the washcoat layer is actually fixed in the pores of the support and not only bound to the outer surface of the monolith channels. This manner of coating is carried out using a solution (or a sol) of the material to be deposited or using a solution comprising very small colloidal particles. The disadvantage of carrying out the coating by filling of the pores is that the amount of coating which can be deposited is limited since the pores become completely filled at some time and the washcoat becomes inaccessible.

Monoliths offer favorable conditions for carrying out the autothermal dehydrogenation of hydrocarbons: in particular, narrower reactor cross sections and higher flow velocities compared to randomly packed fixed beds can be achieved, so that effective, progressive introduction of the oxygen into the hydrocarbon-comprising main stream is possible. The flow direction of the main stream through the reactor is not limited to downward flow, as in the case of randomly packed fixed beds.

After a relatively long period of operation, the catalysts recommended in the present text can normally be regenerated in a simple manner, for example by first passing air which is (preferably) diluted with nitrogen and/or steam through the fixed catalyst bed at an inlet temperature of from 300 to 600° C. (in extreme cases up to 750° C.), frequently from 500 to 600° C., in first regeneration steps. The space velocity of regeneration gas over the catalyst can (based on the total amount of catalyst regenerated) be, for example, from 50 to 10 000 $h^{-1}$ and the oxygen content of the regeneration gas can be from 0.5 to 20% by volume.

It is then generally advisable to continue regeneration using pure molecular hydrogen or using molecular hydrogen diluted with inert gas (preferably steam and/or nitrogen) under otherwise identical conditions (the hydrogen content should be ≥1% by volume).

The monoliths which are stacked next to one another, above one another and behind one another to form a packing are preferably enclosed in an expandable mat or in a mineral fiber nonwoven and inserted in a casing having a clamping device. As mineral fiber nonwovens, preference is given to using nonwovens as are known for use for offgas catalysts, for example Interam® mats from 3M®.

Expandable mats are known from catalytic offgas purification and are described, for example, in DE-A 40 26 566: they consist essentially of ceramic fibers with embedded mica. As a result of the embedded mica, the expandable mat seeks to expand at increasing temperatures, as a result of which the body enveloped therein is held particularly securely even at elevated temperatures.

The mineral nonwovens or expandable mats are selected so that they expand on heating and seal the generally ceramic monoliths against the housing, in particular prevent rubbing of the monoliths against the housing and bypass flow of the reaction gas mixture along the inner wall of the housing.

The expandable mats in which the monoliths are enclosed ensure a stable position of the monoliths since they generate a clamping force when they undergo thermal expansion. However, the clamping force can decrease in the event of incorrect conditions. It can therefore be advantageous to provide a clamping device: for this purpose, the expandable mats are inserted at their end corresponding to the exit for the reaction gas mixture into a U-profile formed by a high-temperature-resistant woven mesh which can, for example, be metallic. Metal profiles which have a cross section corresponding to the cross section of the expandable mats and are attached to the mats and increase in width in the flow direction of the reaction gas mixture are arranged in the extension of the expandable mats. As a result, the metal profiles act as supports to prevent shifting of the expandable mats in the flow direction of the reaction gas mixture.

The monoliths enclosed in expandable mats are arranged in a housing.

The housing is advantageously made of a material which is mechanically and chemically stable at the high reaction temperature, frequently in the range from about 400 to 700° C., and also has no catalytic activity for the autothermal gas-phase dehydrogenation.

The housing is preferably made of a material which is heat-resistant, in particular a stainless steel having the material number 1.4541, 1.4910 or 1.4841.

The housing should be very thin in order to give a very low heat capacity and thus limit the heat losses between the outer region B and the inner region A.

The housing can preferably be thermally insulated.

The housing can preferably be installed unfastened in the reactor.

The housing is preferably configured as a cuboid.

The side walls of the housing configured as a cuboid are preferably configured so as to be removed individually so that a complete packing or individual monoliths of a packing in a catalytically active zone can be replaced.

According to the invention, the individual monoliths are stacked beside one another, above one another and behind one another in the required number in order to fill out a catalytically active zone and form a packing.

At least one mixing zone having fixed internals which are not catalytically active is provided before each packing. Mixing of the hydrocarbon-comprising gas stream with the oxygen-comprising stream occurs in the mixing zone, with mixing of the oxygen-comprising gas stream with the hydrocarbon-comprising feed stream occurring in the first mixing zone in the flow direction and intermediate introduction of an oxygen-comprising gas stream into the hydrocarbon-comprising reaction mixture yet to be dehydrogenated being carried out in each of the subsequent (in the flow direction) mixing zones.

The hydrocarbon-comprising gas stream to be dehydrogenated can preferably be introduced into the heat exchanger at two or more places, in particular as a main stream having a higher mass flow and one or more secondary streams having a lower mass flow compared to the main stream.

To heat the hydrocarbon-comprising gas stream to be dehydrogenated, one or more supplementary heating devices can be provided in addition to the heat exchanger. As supplementary heating, preference is given to introducing hydrogen through the feed line for the hydrocarbon-comprising gas stream to be dehydrogenated as close as possible to the inlet into the mixing zones arranged upstream of each catalytically active zone.

As an alternative or in addition, the supplementary heating can be provided as electric heating which is installed, preferably detachably, as plug-in system, within the outer region B of the reactor in the feed line for the hydrocarbon-comprising gas stream after the latter has exited from the heat exchanger. As an alternative or in addition, a muffle burner can be provided as supplementary heating.

As a result of the reactor being designed as an essentially horizontal cylinder, the inner space A which comprises the monolith packings is supported over a large area and thus subjected to decreased mechanical stress. Furthermore, this reactor design makes accessibility to the individual monolith packings easier.

The outer wall of the reactor is preferably made of an alloy steel approved for pressure vessels, in particular a black steel, preferably Kesselblech HII, or an alloy steel having the material number 1.4541 or 1.4910. The outer wall of the reactor can also be covered with a chamotte lining.

Each mixing zone preferably comprises a tube distributor formed by a plurality of parallel plug-in tubes which are arranged in a plane perpendicular to the longitudinal direction of the reactor and are connected with one or more of the distributor chambers and have a plurality of uniformly spaced outlet openings for exit of the oxygen-comprising gas stream from the plug-in tube, and also a plurality of uniformly spaced mixing elements.

The mixing elements can advantageously be configured as mixing plates.

The heat exchanger is preferably a shell-and-tube heat exchanger.

The shell-and-tube heat exchanger is advantageously made of a highly heat-resistant stainless steel, in particular a stainless steel having the material number 1.4541 or 1.4910. The tubes of the shell-and-tube heat exchanger are advantageously installed at both ends in tube plates without leaving a gap by backplate welding and the tube plates of the shell-and-tube heat exchanger are clad on the hot gas side of the plates with a heat-resistant stainless steel, in particular a stainless steel having the material number 1.4841.

A flow straightener is preferably arranged at the end face of the housing G at which the hydrocarbon-comprising gas stream is introduced into the inner region A.

The invention also provides a process for carrying out autothermal dehydrogenations using the above-described reactors.

In a preferred, fully continuous mode of operation, two or more reactors can be used, with at least one reactor being utilized for the autothermal gas-phase dehydrogenation and at the same time at least one further reactor being regenerated.

The regeneration is preferably carried out in a temperature range from 550 to 700° C.

The regeneration is also preferably carried out using an oxygen-comprising gas stream having an oxygen content in the range from 0.1 to 1.5% by weight of oxygen, based on the total weight of the oxygen-comprising stream.

To operate the raffinate II process economically, periodic regeneration of the carbonized catalyst is advantageous. In preliminary studies, the periodic operation was carried out in a miniplant and a regeneration procedure which allows cycle-stable productivity was developed. The dehydrogenation phase and the regeneration phase each take about 12 hours. Quasicontinuous production using two alternately operated reactors is therefore possible.

At the beginning of the regeneration operation, the catalyst is at the operating temperature and the operating pressure when the dehydrogenation is switched off. The dehydrogenation gas mixture is still enclosed in the gas space. In a flushing step, the reaction mixture is driven out by means of a stream of nitrogen.

The carbonaceous material is subsequently burnt off. For this purpose, lean air, diluted with nitrogen, is passed over the catalyst. The burning-off of the carbonaceous deposits requires rigid temperature control, since the burning-off operation has to occur within a temperature window from 550 to 700° C.; at lower temperatures, residual carbonaceous material remains on the catalyst. Temperatures which are too high accelerate the irreversible thermal deactivation of the catalyst. The burning-off operation can be recognized by formation of a temperature front which slowly migrates in the flow direction and the formation of $CO_2$. At the end of burning-off, the oxygen breaks through and the oxygen concentration increases. A smooth transition to the redispersion phase therefore takes place.

Redispersion of the catalyst is intended to repair the deactivation caused by coalescence of the catalyst crystallites. For this purpose, air having a temperature of about 550° C. is passed over the catalyst. It is presumed that as a result the active component (a Pt/Sn alloy) is oxidized and wets the support as a liquid oxide film. The duration of the redispersion depends on the duration of the complete regeneration cycle.

After redispersion, the catalyst has to be reactivated by reduction. At the same time, the reactor is conditioned for the subsequent production phase. This operation comprises the following steps:
  a. The oxygen is driven out from the reactor. For this purpose, the reactor is flushed with nitrogen or $H_2O$ vapor at about 500° C.
  b. Reduction of the catalyst is carried out by means of a mixture of steam and hydrogen in a volume ratio of 15:85 at about 500° C.
  c. The dehydrogenation is started.

The autothermal gas-phase dehydrogenation is preferably a dehydrogenation of propane, of butene, of isobutene, of butene to butadiene or of ethylbenzene to styrene.

The reactor according to the invention and the process according to the invention have in particular the advantages that optimized reactor arrangement with respect to mechanical loading, handling and connection to peripheral apparatuses, safe control of the combustible reaction media with avoidance of temperature peaks and corresponding stressing of materials and also simple accessibility and handling of the individual monoliths are ensured. In addition, the reactor arrangement according to the invention makes optimal main and intermediate introduction of oxygen possible.

The autothermal gas-phase dehydrogenation is particularly preferably the dehydrogenation of butane, in which two reactors as described above are used and one reactor is utilized for the autothermal gas-phase dehydrogenation while at the same time a second reactor is being regenerated.

Raffinate II, which generally comprises 70% by weight of butenes and 30% by weight of n-butanes, is produced by dehydrogenation of butane.

The main reactions are described by the following stoichiometric equations:

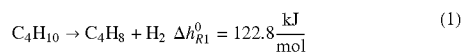

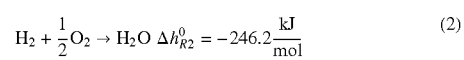

A Pt/Sn system is used as catalyst.

Under industrially relevant conditions, the main reaction (1) achieves a partial conversion. The unreacted butane and part of the dehydrogenation hydrogen have to be separated off from the product stream and recirculated to the reactor. For this reason, the reaction step is coupled with a sequence of work-up steps.

The reactor is designed as a tray reactor having three catalytically active layers. The hydrocarbon-comprising gas stream (feed stream) comprises fresh butane, steam and a butane-rich return stream and a hydrogen-rich return stream from the work-up. Before each catalytically active zone, there is a side inlet via which oxygen, diluted with steam, is mixed into the main stream. In a narrow zone at the entrance to the catalytically active layer, the reaction mixture is heated by selective partial combustion of the dehydrogenation hydrogen. Further on, the heat is consumed by the dehydrogenation reaction and the reaction mixture cools. This gives a saw-tooth-shaped temperature profile between 500 and 650° C. along the reactor.

The optimal operating pressure is from 1.5 to 2 bar absolute.

Under these conditions, the target reaction (1) achieves a conversion of about 40% and a selectivity of >95%. The most important secondary reactions are:

Total Oxidation of Butane:

Various Dissociation Reactions:

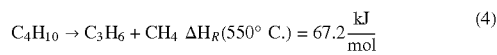

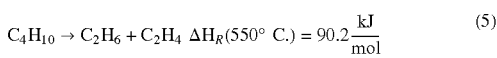

Product Dehydrogenation:

The dehydrogenation of adsorbed hydrocarbons can also proceed to carbonization, formally:

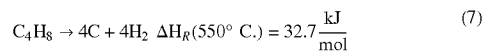

Further secondary reactions which do not have a direct effect on the product selectivity are the water gas shift reaction:

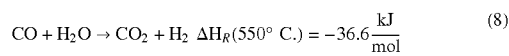

and the Bouduard reaction:

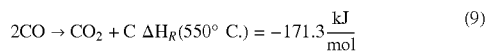

Under the operating conditions indicated, the catalyst becomes coated with carbon deposits within a few hours and loses its initial activity. The carbonization is indicated by the increase in the temperature level.

To operate the process economically, periodic regeneration of the carbonized catalyst is therefore necessary.

In the production mode of the autothermal gas-phase dehydrogenation, the reactor is operated until normal reactor operation is no longer possible because of carbonization of the catalyst, whereupon the reactor is switched over to the regeneration mode. At the same time, a second reactor of the same type is switched over from the regeneration mode to the production mode of the autothermal gas-phase dehydrogenation.

In particular, the production mode and the regeneration mode are each operated for 12 hours. This makes pseudocontinuous operation with two alternately operated reactors possible.

The regeneration comprises the following process steps:

1. Making Inert (Flushing) of the Reactor

At the beginning of the regeneration mode, the catalyst is at the operating temperature and the operating pressure on shutting down the autothermal gas-phase dehydrogenation. The dehydrogenation gas mixture is still present in the gas space. In the first regeneration step (making inert or flushing), the reaction gas mixture is driven out by, in particular, a stream of nitrogen.

2. Burning-Off

In the next regeneration step, viz. the burning-off of the carbon deposits on the surface of the heterogeneous catalyst, lean air, diluted with nitrogen, is passed over the catalyst. The burning-off of the carbon deposits requires rigid temperature control since the burning-off process has to proceed within a temperature window from 550 to 700° C.: at lower temperatures, a residual loading remains on the catalyst. Excessively high temperatures accelerate the irreversible thermal deactivation of the catalyst. The burning-off process is recognizable by formation of a temperature front which migrates slowly in the flow direction and the formation of $CO_2$. At the end of burning-off, the oxygen breaks through and the oxygen concentration increases. A smooth transition to the redispersion phase thus takes place.

3. Redispersion

The redispersion (process step 3) of the heterogeneous catalyst is intended to reverse the deactivation caused by coalescence of the catalyst crystallites. For this purpose, air is passed over the catalyst at a temperature of about 550° C. It is presumed that this results in the active component (a Pt/Sn alloy) being oxidized and wetting the support with a liquid oxide film. The dispersion of the catalyst over the support surface is indicated by the degree of distribution. The degree of dispersion is defined as the proportion of atoms of the active substance which are in direct contact with the surface. Accordingly, the degree of dispersion of a monolayer would be 100%. The degree of dispersion cannot be measured directly and can only be accessed via the performance of the catalyst in the dehydrogenation cycle.

4. Flushing

Redispersion is followed in the next process step by flushing of the heterogeneous catalyst and finally a further process step, viz.

5. Reduction of the Heterogeneous Catalyst in Order to Reactivate the Latter.

At the same time, the reactor is conditioned for the subsequent production phase. This conditioning comprises the following steps:

a. The oxygen is driven from the reactor. For this purpose, the reactor is flushed with nitrogen or steam at about 500° C.
b. The catalyst reduction is effected by means of a mixture of steam and hydrogen in a volume ratio of 15:85 at about 500° C.
c. The hydrogenation is started.

The relevant operating states for a reactor for the autothermal gas-phase dehydrogenation of butane are described in detail below:
1. First start-up of the reactor
2. Start-up of the reactor after it has been down
3. Cyclic production operation with the following operating modes:
   3.1 Production mode
   3.2 Regeneration mode
      a. Flushing
      b. Burning-off
      c. Oxidation/redispersion
      d. Flushing
      e. Reduction
4. Shutdown of the reactor
5. Emergency shutdown in the event of a malfunction.

1. First Start-Up and 2. Start-Up of the Reactor after it has been Down

The start-up procedure should establish the initial state for periodic operation. It commences when the reactor, the feed lines and the discharge line have been preheated and flooded with steam. This mainly requires setting of a suitable temperature level in the reaction section, i.e. in the catalytically active zones.

For this purpose, the feed is heated from 200° C. to about 500° C. in the heat exchanger. The temperature in the reaction section is 550° C.

In particular, two possibilities of preheating the reaction section are provided:

reactive heating by catalytic combustion of hydrogen:
   Hydrogen is used as fuel gas since the combustion of hydrogen is ignited spontaneously on the Pt/Sn catalyst above the preheated temperature. The reactor is operated in the recycle mode. Air is introduced into the circuit via the main stream. Hydrogen is introduced via the side stream and mixed with the main stream in a stoichiometric ratio of oxygen to hydrogen which ensures complete consumption of the hydrogen. The heating-up procedure takes about twelve hours. At the end of this phase, the reaction section has reached a temperature level of 550° C.

Auxiliary heating in the main stream:
   A connection for auxiliary heating is provided in the line to the entrance into the reaction section. Electric heating, a muffle burner or a recuperative burner can be installed as required in this section of the line. A small stream of nitrogen is introduced into the circuit via the main line.

Reactive heating has the advantage that the heat is liberated directly out of the catalyst. Heat losses can be minimized in this way. In addition, the procedure does not require any additional apparatus. The use of hydrogen is advantageous because its catalytic combustion commences spontaneously and without auxiliary heating above 200° C. A disadvantage is that incorrect metering of the fuel can lead to overheating of the catalyst, in the worst case also to formation of an ignitable mixture. In addition, reactive heating requires a sufficiently active catalyst. However, this prerequisite is not ensured, for example when the catalyst is strongly carbonized.

The use of external auxiliary heating (electric heating or burners) increases the reliability of the procedure. Electric preheating in particular offers the advantage that the catalyst can be preheated to the reaction temperature in a mild, inert atmosphere. The outlay for regulation and safety is considerably reduced in this way. Disadvantages of external auxiliary heating is the additional apparatus required and the operating costs (applies to electric heating). A process engineering disadvantage results from the distance between the heat source and the catalyst. The heat losses in the section of the line in between have to be compensated in order to achieve the desired catalyst temperature.

The heating phase is followed by a conditioning phase. This commences when the reaction section has been heated to 550° C., a steady-state, approximately linear temperature profile between the feed stream temperature and the reaction temperature has been established in the heat exchanger and the reactor volume has been flooded with inert gas (nitrogen or steam).

The conditioning procedure is intended to convert the catalyst into a defined, active state before commencement of production operation. The conditioning comprises a reduction-oxidation-reduction sequence (also referred to as ROR procedure). The first reduction step serves mainly to reduce volatile Pt salts. These salts, in particular platinum(IV) chloride, can be residues from the preparation of the catalyst. In the oxidation step, possible organic deposits are burnt off from the catalyst surface and the catalyst crystallites are redispersed.

The catalyst is activated in the subsequent reduction step.

3.1 Production Mode

In the initial state, the temperature in the reaction section is about 550° C., and an approximately linear temperature profile between the feed stream temperature and the reaction temperature has been established in the heat exchanger. The catalyst is in its reduced, active state and is free of carbon deposits. The reaction volume is filled with hydrogen/steam. The pressure is 1.5 bar (a), measured at the reactor outlet.

The reactor is operated in a single pass. In the main stream 4001, the starting material for the dehydrogenation is fed in.

Apart from the components listed, trace components can optionally be added. The following table indicates the range in which the concentration of the trace components should be varied.

Concentration range of the trace components in the feed stream during the dehydrogenation

| Component | Proportion by volume |
|---|---|
| $C_4H_6$ | 0-0.5% |
| $CH_4$ | 0-2.0% |
| CO | 0-5.0% |
| CO | 0-0.5% |
| NMP | 0-500 ppm |

The proportion of the main components will be reduced in accordance with the amount of further material mixed in. The oxygen-comprising streams required to supply heat to the autothermal dehydrogenation are introduced via the side inlets. The proportion of oxygen is 15% by volume in a carrier stream of steam.

The set value for the pressure at the exit of the reaction section is set to 1.5 bar (a). At desired loads, the following pressure profile is established over the reaction section (in each case at the entrance to the catalytically active zone):

| | |
|---|---|
| first catalytically active zone: | 2.0 bar |
| second catalytically active zone: | 1.87 bar |
| third catalytically active zone: | 1.70 bar |

In the heat exchanger, the tube-side (product-side) pressure drop is <15 mbar, and is thus negligible compared to the pressure drop in the reaction section.

The temperature profile in the catalytically active zone displays the typical sawtooth shape due to the intermediate introduction of oxygen. In the heat exchanger, a slightly convex temperature profile is established because of the higher heat capacity stream on the product side compared to the feed side. The temperature level increases continuously during the dehydrogenation phase. The reason for this is the accumulation of carbon deposits on the catalyst. The carbon deposits lead to deactivation of the catalyst, as a result of which the heat consumption of the dehydrogenation reaction has a downward tendency. As a consequence, the exit temperature from the catalytically active zone increases and the driving temperature difference in the heat exchanger therefore also increases. This brings about an increase in the preheating temperature. The decrease in activity is largely compensated by the increase in the temperature level. The deactivation thus has only a slight influence on the final conversion. This self-adapting behavior of the heat-integrated system substantially simplifies the operation of the process since no additional oxygen has to be introduced to maintain the production rate.

| | |
|---|---|
| Upper flow limitation: | |
| Pressure drop in the reaction section: | $\Delta p_{1001 \rightarrow 1010}$ < 700 mbar |
| Velocity in the narrowest cross section: | $v_{max}$ < 60 m/s |
| Lower flow limitation: | |
| Residence time in the mixing zone: | $\tau_{mix}$ < 100 ms |
| Re number in the mixing zone: | Re > 6000 |
| Temperature limitation in the mixing zones: | $T_{mix}$ < 550° C. |
| Limitation by heat losses: | $\Delta T_{loss}$ < 20 K |

$\Delta T_{loss}$ is the decrease in temperature at the output from the reaction section compared to an adiabatic measurement section.

The flow limitations result from the reactor construction. The temperature limitation in the mixing zones is set in order to avoid selectivity losses due to ignition of the homogeneous combustion. The limitation of the heat losses is intended to limit falsification of the operating state.

At the given composition of the feed streams, the above limits give the following permitted load range for the reactor:

| Stream | | MIN | MAX |
|---|---|---|---|
| Main stream (4001) | | 540 kg/h (350 standard m³/h) | 925 kg/h (600 standard m³/h) |
| Side streams | 5004 | 77 kg/h (86 standard m³/h) | 132 kg/h (148 standard m³/h) |
| | 5002 | 44 kg/h (49 standard m³/h) | 76 kg/h (85 standard m³/h) |
| | 5003 | 32 kg/h (36 standard m³/h) | 55 kg/h (62 standard m³/h) |

3.2 Regeneration Mode

The periodic regeneration of the catalyst is a complex procedure which comprises a number of phases. The time sequence of the regeneration steps is shown in the following table.

| Phase | Duration (approx.) | Operating mode |
|---|---|---|
| a. Flushing (making inert) | 5 min | Single pass |
| b. Burning-off | 4 h 30 min | Recycle mode |
| c. Redispersion | 5 h 55 min | Recycle mode |
| d. Flushing | 30 min | Recycle mode |
| e. Reduction | 1 h | Recycle mode | a. Flushing (Making Inert)

In the making inert depth, the reactor volume is replaced at least five times by nitrogen. This is intended to drive out residues of the reaction gas mixture from the dehydrogenation.

b. Burning-Off

The burning-off of the carbon deposits on the catalyst surface is the central regeneration step in order to restore the catalyst activity. This step places particular demands on the regulation of the process. The task in terms of regulation can be formulated as follows: the carbon loading should be eliminated in a minimum time and at a minimum temperature level. The basic difficulty with this task is that neither the carbon loading on the catalyst nor the burning-off rate can be measured directly. Modeling thereof is based primarily on adaptations of miniplant experiments. Further information is given by thermogravimetric analyses of samples of carbonized catalysts removed from the reactor. These indicate two types of carbon deposits which differ morphologically or in terms of composition. In the TGA graph, combustion of the first fraction commences at about 550° C. and displays the typical, exponential acceleration versus temperature. The signal drops abruptly at 580° C. and continues with a significantly flatter gradient up to about 630° C. This observation is consistent with the results of spectroscopic analyses for the hydrogenation of propane over model catalysts.

The available information is not sufficient for a knowledge-based design of the regeneration. Rather, heuristic procedure is followed, employing the temperature profile and the oxygen consumption as substitute regulated variables. The assignment of regulated variables and controlled variables is summarized in the following table.

Regulated variables and controlled variables for the burning-off of the carbon deposits

| Regulated variables | Controlled variables |
|---|---|
| Maximum temperature | Oxygen concentration |
| Duration of the burning-off process | Amount of oxygen |
| Speed of burning-off | Catalyst temperature |
| Equal distribution of the flow | Volume flow |

Simulation studies show that the regulated variables are influenced in a complicated way by all controlled variables. In addition, the maximum temperature cannot be controlled directly because of the localized distribution. The concept for regulation therefore has to be made rougher: the burning-off process is no longer state-controlled but time-controlled.

The single regulatable variable is the entry temperature of the gas stream into the reaction zone with a set value: $T_{in}^{set}=570°$ C. Controlled variables for this are the introduction of an auxiliary gas if the temperature goes below the set value and a bypass stream round the heat exchanger if the set value is exceeded. The amount of oxygen and the oxygen concentration are set empirically to fixed values. Gas recirculation is activated.

The carbon deposits can be removed completely within five hours using the chosen settings. The first and second zones are regenerated simultaneously, while the throughput in the third zone is initially largely maintained. The deposits are removed uniformly over the length of the respective zone. Only toward the end of the regeneration phase are the deposits removed in a wave-like fashion in the third zone.

The positive back-coupling by means of the integrated back-exchange of heat brings about an "excitable" behavior of the reaction section. The maximum temperature cannot be regulated to any set value. On the other hand, maintenance of a set value for the maximum temperature is not necessary. The regeneration can be carried out in an oxygen-limited manner with a fixed introduction of oxygen. The temperature profile changes in a wave-like fashion, so that local temperature peaks are only briefly active. Overheating of the catalyst is usefully prevented by a switch when an upper temperature limit is exceeded. This interrupts the oxygen supply. In this case, the temperature peak has to be pushed out of the reaction zone by the inert carrier gas stream.

The circulation of the regeneration gas has many advantages for the control of the burning-off process. An obvious advantage is minimization of the inert gas consumption required to achieve the necessary dilution of the oxygen. A further advantage is the automatic adaptation of the oxygen concentration in the circuit. In the configuration under consideration, the oxygen concentration varies from 0.52% by weight in the case of complete oxygen consumption to 6.97% by weight at complete retention of the oxygen. The increase in oxygen concentration promotes the ignition of the carbon deposits at the beginning of the regeneration. At the end of the phase, the oxygen concentration increases in a ramp-like fashion and brings about a continuous transition to the subsequent redispersion using undiluted air.

c. Oxidation (Redispersion) of the Heterogeneous Catalyst

The redispersion of the catalyst is carried out using air. For this purpose, an auxiliary gas is introduced in order to regulate the temperature in the reaction zone. Here, any residual deposits present can be removed from the catalyst surface.

The duration of this phase is adapted so as to achieve synchronization between the production mode and the regeneration mode. This phase is also suitable for stand-by operation of the reactor.

d. Flushing

During the flushing phase, the reactor is made inert in order to rule out mixing of oxygen-comprising gases from the redispersion phase with hydrogen-comprising gases from the subsequent reduction phase.

e. Reduction

The main function of the reduction phase is to convert the partially oxidized catalyst components into the metallic, catalytically active state. At the same time, the shape of the crystallites is fixed after the redispersion. In addition, the temperature profile has to be set for the start of production. Here, a temperature level of about 500° C. is sought in the catalytically active zones. As a result of the integrated recirculation of heat, cooling is so slow that in the final state the temperature level in the catalytically active zones is still significantly above the set value. This state can be corrected by temperature regulation: when the set value is exceeded, the bypass on the heat exchanger can be opened. When the temperature goes below the set value, oxygen can be introduced in a substoichiometric amount via the side inlet, resulting in part of the hydrogen being burnt.

With the recycle gas cooler switched off, the temperature at the cold end of the heat exchanger increases to about 350° C. This value corresponds to the temperature in the recirculation loop. This threatens to overheat the recycle gas blower. On the other hand, with the recycle gas cooler switched on, the temperature is controlled in a targeted manner to about 200° C. In this way, thermal stressing of the apparatuses and fittings in the circuit can be reduced or the specification for these components can be relaxed.

The invention makes it possible to carry out autothermal gas-phase dehydrogenations at lower capital and operating costs and to utilize monolith catalysts at higher loading and improved selectivity for autothermal gas-phase dehydrogenations.

The invention is illustrated below with the aid of an example and a drawing.

Figure 4:
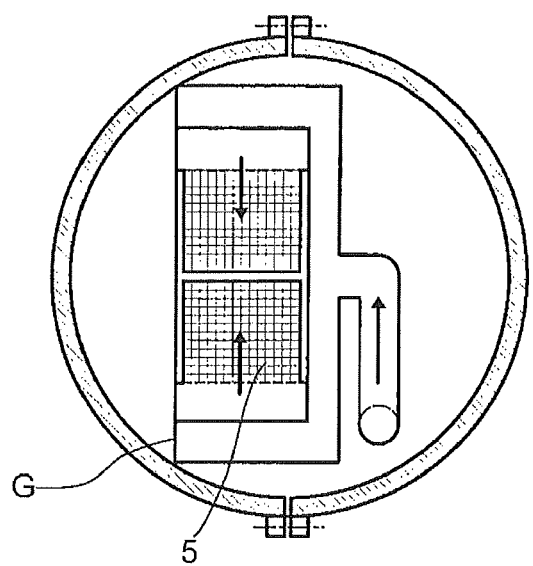
Figure 5:
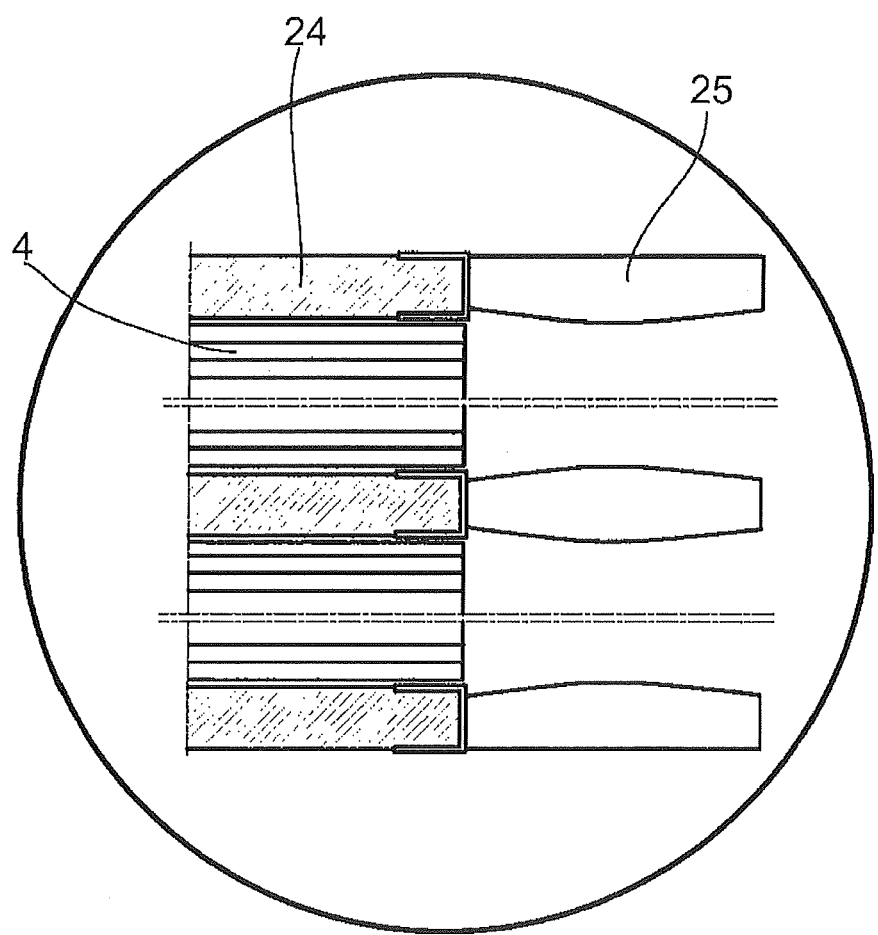

In the drawing:

FIG. 1 shows a longitudinal section through a preferred embodiment of a reactor according to the invention in the horizontal plane, FIG. 2 shows a longitudinal section through the same reactor in the vertical plane, FIG. 3 shows a cross section through the reactor shown in FIG. 2 in the plane B-B, FIG. 4 shows a cross section through the reactor shown in FIG. 2 in the plane A-A and FIG. 5 shows an enlargement of the encircled region in FIG. 1.

Identical reference numerals in the figures in each case denote identical or corresponding features.

The longitudinal section in the horizontal plane in FIG. 1 schematically shows a preferred embodiment of a reactor 1 according to the invention which is supplied with a hydrocarbon-comprising gas stream 2 to be dehydrogenated via a feed line 11 and with an oxygen-comprising gas stream 3 via the feed lines 9. FIG. 1 shows that the housing G divides the interior of the reactor 1 into an inner region A and an outer region B. The inner region A is adjoined at one end by a heat exchanger 12. Feed lines 20 for the purge gas stream are shown at the right-hand side of the drawing and a connecting line 21 for the purge gas stream from the outer region B of the reactor into the feed line 7 for the hydrocarbon-comprising gas stream 2 to be dehydrogenated is shown on the left-hand side. A purge gas stream is introduced via the feed lines 20 into the outer region B and conveyed further via a connecting line 21 at the other end of the reactor via the feed line 7 for the hydrocarbon-comprising gas stream 2 to be dehydrogenated into the inner region A.

The figure shows supplementary heating devices which can advantageously be used: electric heating 22 and also a feed line 23 for hydrogen as fuel gas into the feed line 7 for the hydrocarbon-comprising gas stream 2 to be dehydrogenated.

FIG. 3 shows a cross-sectional depiction of the plane B-B in the region of the heat exchanger. The figure shows the introduction of the hydrocarbon-comprising gas stream 2 to be dehydrogenated via the feed line 7 into the intermediate space between the tubes 17 of the preferred embodiment of a shell-and-tube heat exchanger 12 shown in the figure.

In the cross-sectional depiction, it is likewise possible to see the support construction 18 for the shell-and-tube heat exchanger 12, which support construction is preferably formed from perforated plates, the layer of insulation 19 on the inner wall of the reactor jacket and the electric heating 22 which is preferably used as supplementary heating.

FIG. 4 shows a further cross-sectional depiction in the plane A-A in the region of a reaction zone. The figure shows, in particular, the feed line 23 for fuel gas.

The enlargement shown in FIG. 5 illustrates the steel profiles 25 which are, in the extension of the expandable mats 24, inserted in U-profiles of high-temperature-resistant woven meshes, and, with a cross section corresponding to that of the expandable mats 24, adjoin the mats and become increasingly wider. The reference numeral 4 in FIG. 5 denotes the monoliths.

The invention claimed is:

1. A reactor in the form of an essentially horizontal cylinder or prism for carrying out an autothermal gas-phase dehydrogenation of a hydrocarbon-comprising gas stream by means of an oxygen-comprising gas stream to give a reaction gas mixture over a heterogeneous catalyst configured as monolith, where
the interior of the reactor is divided by a cylindrical or prismatic gastight housing G which is arranged in the longitudinal direction of the reactor into
an inner region A having one or more catalytically active zones, in which a packing composed of monoliths stacked on top of one another, next to one another and behind one another and before each catalytically active zone in each case a mixing zone having solid internals are provided, and
an outer region B arranged coaxially to the inner region A, and
a heat exchanger is provided at one end of the reactor connected to the housing G,
with one or more feed lines for the hydrocarbon-comprising gas stream to be dehydrogenated,
with one or more feed lines which can be regulated independently of one another, where each feed line supplies one or more distribution chambers, for the oxygen-comprising gas stream into each of the mixing zones and with a discharge line for the reaction gas mixture of the autothermal gas-phase dehydrogenation,
wherein
the outer region B is supplied with a gas which is inert under the reaction conditions of the autothermal gas-phase dehydrogenation and
the hydrocarbon-comprising gas stream to be dehydrogenated is introduced via a feed line into the heat exchanger, is heated in the heat exchanger by means of the reaction gas mixture in countercurrent by indirect heat exchange and conveyed further to the end of the reactor opposite the heat exchanger, redirected there, introduced via a flow equalizer into the inner region A and mixed with the oxygen-comprising gas stream in the mixing zones, whereupon the autothermal gas-phase dehydrogenation takes place in the inner region A of the reactor.

2. The reactor according to claim 1, wherein the gas which is inert under the reaction conditions of the autothermal gas-phase dehydrogenation is steam.

3. The reactor according to claim 1, wherein the gas which is inert under the reaction conditions of the autothermal gas-phase dehydrogenation is passed as a purge gas stream at a mass flow of from $\frac{1}{5}$ to $\frac{1}{100}$, based on the mass flow of the hydrocarbon-comprising gas stream under a slight gauge pressure of from 2 to 50 mbar, based on the pressure in the inner region A, through the outer region B, preferably by introducing the purge gas stream via one or more feed lines into the outer region B of the reactor at one end of the reactor and conveying it further into the inner region A of the reactor at the opposite end of the reactor, in particular via one or more connecting line(s) which are advantageously arranged at an angle other than 90° to the feed line for the hydrocarbon-comprising gas stream to be dehydrogenated.

4. The reactor according to claim 1, wherein the hydrocarbon-comprising gas stream to be hydrogenated is introduced into the heat exchanger at two or more places, as a main stream having a higher mass flow and one or more secondary streams having a lower mass flow compared to the main stream.

5. The reactor according to claim 1, wherein one or more supplementary heating devices for the hydrocarbon-comprising gas stream to be dehydrogenated are provided in addition to the heat exchanger.

6. The reactor according to claim 5, wherein introduction of hydrogen via a line into the feed line for the hydrocarbon-comprising gas stream to be dehydrogenated, as close as possible to the inlet into the mixing zones which are arranged upstream of each catalytically active zone, is provided as supplementary heating for the hydrocarbon-comprising gas stream.

7. The reactor according to claim 5, wherein electric heating which is installed detachably, as plug-in system, within the outer region B of the reactor or as muffle burner into the feed line for the hydrocarbon-comprising gas stream to be dehydrogenated after the latter has exited from the heat exchanger is provided as supplementary heating.

8. The reactor according to claim 1, wherein two or more catalytically active zones each having a packing composed of monoliths stacked on top of, next to and behind one another are provided in the inner region A.

9. The reactor according to claim 8, wherein the two or more catalytically active zones have in each case a different catalytic activity.

10. The reactor according to claim 1, wherein the monoliths within the same catalytically active zone have in each case a different catalytic activity.

11. The reactor according to claim 1, wherein the monoliths which are stacked next to, above and behind one another to form a packing are enveloped in an expandable mat or a mineral fiber nonwoven and installed in a housing with a tensioning device.

12. The reactor according to claim 1, wherein the housing G is configured as a prism, and the side walls of the housing G configured as a prism can be taken off individually so that a complete packing or individual monoliths of a packing from a catalytically active zone can be replaced.

13. The reactor according to claim 1, wherein the housing G is made of a material which is heat-resistant.

14. The reactor according to claim 1, wherein the outer wall of the reactor is made of a nonalloy or low-alloy steel approved for pressure vessels.

15. The reactor according to claim 1, wherein each mixing zone comprises a tube distributor formed by a plurality of parallel plug-in tubes which are arranged in a plane perpendicular to the longitudinal direction of the reactor and are connected to one or more of the distributor chambers and have a plurality of uniformly spaced outlet openings for the oxygen-comprising gas stream from the plug-in tube and also a plurality of uniformly spaced mixing elements.

16. The reactor according to claim 15, wherein the mixing elements are configured as mixing plates.

17. The reactor according to claim 1, wherein a shell-and-tube heat exchanger which is made of a highly heat-resistant stainless steel and whose tubes are installed at both ends of the tubes in tube plates without leaving a gap by backplate welding and whose tube plates are clad on the hot gas side of the heat exchanger with a heat-resistant stainless steel, is used as heat exchanger.

18. A process for carrying out an autothermal gas-phase dehydrogenation using one or more reactors according to claim 1.

19. The process according to claim 18, wherein two or more reactors according to claim 1 are used, with at least one reactor being utilized for the autothermal gas-phase dehydrogenation and at least one further reactor being regenerated at the same time.

20. The process according to claim 19, wherein the regeneration is carried out in a temperature range from 550 to 700° C.

21. The process according to claim 19, wherein the regeneration is carried out using an oxygen-comprising gas stream comprising from 0.1 to 1.5% by weight of oxygen, based on the total weight of the oxygen-comprising gas stream.

22. The process according to claim 18, wherein the autothermal gas-phase dehydrogenation is a dehydrogenation of propane, of butane, of isobutane, of butene to butadiene or of ethylbenzene to styrene.

23. The process according to claim 22, wherein the autothermal gas-phase dehydrogenation is the dehydrogenation of butane and two reactors are used, with one reactor being utilized for the autothermal gas-phase dehydrogenation and at the same time a second reactor being regenerated.

24. The process according to claim 23, wherein the regeneration comprises the following process steps:
   making-inert of the reactor,
   burning-off of the carbon deposits on the surface of the heterogeneous catalyst,
   redispersion of the heterogeneous catalyst by means of air,
   flushing of the heterogeneous catalyst and
   reduction of the heterogeneous catalyst.

* * * * *